(12) United States Patent
Gentile et al.

(10) Patent No.: US 7,442,832 B2
(45) Date of Patent: Oct. 28, 2008

(54) PAINLESS INJECTABLE COMPOSITIONS CONTAINING SALTS OF 2-ARYLPROPIONIC ACIDS

(75) Inventors: Marco Maria Gentile, L'Aquila (IT); Maria Concetta Dragani, L'Aquila (IT)

(73) Assignee: Dompé S.p.A., L'Aquila (TW)

( * ) Notice: Subject to any disclaimer, the term of this patent is extended or adjusted under 35 U.S.C. 154(b) by 0 days.

(21) Appl. No.: 10/531,579

(22) PCT Filed: Oct. 22, 2003

(86) PCT No.: PCT/EP03/11689

§ 371 (c)(1),
(2), (4) Date: Oct. 12, 2005

(87) PCT Pub. No.: WO2004/037242

PCT Pub. Date: May 6, 2004

(65) Prior Publication Data

US 2006/0058386 A1    Mar. 16, 2006

(30) Foreign Application Priority Data

Oct. 25, 2002 (EP) .................................. 02023954

(51) Int. Cl.
*C07C 59/76* (2006.01)
*C07C 63/33* (2006.01)

(52) U.S. Cl. ....................................... 562/460; 562/491

(58) Field of Classification Search ................. 562/405, 562/491, 459, 460, 462, 490, 492
See application file for complete search history.

(56) References Cited

U.S. PATENT DOCUMENTS 5,895,789 A * 4/1999 Gentile et al. ............... 514/570
6,342,530 B1 * 1/2002 Darko ......................... 514/561

FOREIGN PATENT DOCUMENTS

WO    WO-97/24114 A1    7/1997

OTHER PUBLICATIONS

Anacardio et al., Physicochemical compatibility between ketoprofen lysine salt injections (Artrosilene®) and pharmaceutical products frequently used for combined therapy by intravenous administration, Journal of Pharmaceutical and Biomedical Analysis vol. 32, Issue 6 , Aug. 21, 2003, pp. 1235-1241.*
G.A. Brazeau et al., Journal of Pharmaceutical Sciences, vol. 87, No. 6, Jun. 1998, pp. 667-677.
J. Scott et al., Pain, vol. 2, 1976, pp. 175-184.

* cited by examiner

*Primary Examiner*—Karl J Puttlitz
(74) *Attorney, Agent, or Firm*—Birch, Stewart, Kolasch & Birch, LLP

(57) ABSTRACT

The invention relates to pharmaceutical compositions of alkylammonium salts of 2-aryipropionic acids, including ketoprofen, ibuprofen, naproxen and tiaprofenic acid. The compositions are suitable for parenteral administration arid, due to buffering at pH 8 to 9, cause less pain upon injection than previously known composition.

5 Claims, 2 Drawing Sheets

PAINLESS INJECTABLE COMPOSITIONS CONTAINING SALTS OF 2-ARYLPROPIONIC ACIDS

The present invention relates to pharmaceutical compositions suitable for parenteral administration, which contain alkylammonium salts of 2-arylpropionic acids and which generate no pain upon injection. In particular, the compositions contain ketoprofen, ibuprofen or naproxen in alkaline aqueous solutions.

BACKGROUND OF THE INVENTION

A common limitation in the administration of parenteral products is the onset of pain in the site of injection, that may result from the active drug, the formulation components, or the total formulation. In the development of a parenteral product the attention is mainly focused on the chemical, physical and microbiological stability and on the general safety of the formulation, considering the route of administration, while pain at injection site, that is a negative peculiarity of injectable drug formulations, do not receive much consideration. This is mainly due to the lack in the number and type of models available to study the physiology and mechanisms of pain, the difficulty, variability and cost associated with the use of animal models to evaluate pain and the necessity to use subjective versus objective measures (which often involve extensive experimental set-ups) to evaluate the extent of pain either in animals or humans.

It is possible that a given formulation can cause tissue damage that results in pain at the injection site; in this case toxicity screening methods, like red blood cells hemolysis, or L6 myoblast cell line method, or the rodent in vivo muscle model, can give a rational approach to develop and select the optimal formulations with respect to the desired physico-chemical properties and tissue tolerability (Brazeau G. A. et al., "Current perspectives on pain upon injection of drug", Journal of Parm. Sciences, 87, 6, Jun. 1998).

If, in contrast, there is no indication of any type of tissue damage at the site of injection, before testing any injectable formulations in humans, it is useful to have methods to screen formulations early during development, for their potential to cause pain.

One of these methods is the rat paw-lick model, used as a rapid in vivo screening method for parenteral products, but not always results are obtained, which are subsequently confirmed by clinical data.

BRIEF DESCRIPTION OF THE INVENTION

During our experiments in animals, we have observed that solutions containing ketoprofen at different pH and composition, when instilled in rat's eye, cause reaction in animals by means of an increased number of winks, if compared with instillation of water for injection alone. Supposing that winks are somehow related to pain upon injection, the rat wink test may be used as an alternative animal model for the evaluation of the extent of pain caused by injectable pharmaceutical compositions.

In humans, a well known clinical method of evaluating the painfulness of injectable solutions uses the VAS (Visual Analogue Scale) value as an index (Scott and Huskinsson, Pain, 2:175-184, 1976). VAS number is an evaluation of the intensity of pain at the injection site immediately after injection and after some lag times in humans; the result is expressed using the 100 mm Visual Analogue Scale.

Clinical studies have thus been performed using two ketoprofen injectable compositions at optimum pH, which had caused less pain in the rat wink test. The evaluation of pain upon injection has been performed in comparison with a classical formulation of ketoprofen in phosphate buffer at pH 6.5 and with the commercial preparation "Artrosilene® fiale", ampoules for injection (Dompé farmaceutici S.p.A.) containing ketoprofen lysine salt in an aqueous solution at pH adjusted between 7 and 7.5 with citric acid and sodium hydroxide, and not containing co-solvents, such as benzyl alcohol, which are usually used in injectable formulations to decrease pain upon injection (WO 97/24114).

"Artrosilene® fiale" is known to cause less pain upon injection than the classical formulations of ketoprofen.

We have now found that compositions for parenteral administration containing alkylammonium salts of 2-arylpropionic acids, such as ketoprofen, ibuprofen, naproxen or tiaprofenic acid, in alkaline aqueous solutions do not cause any pain upon injection.

Figure 1:
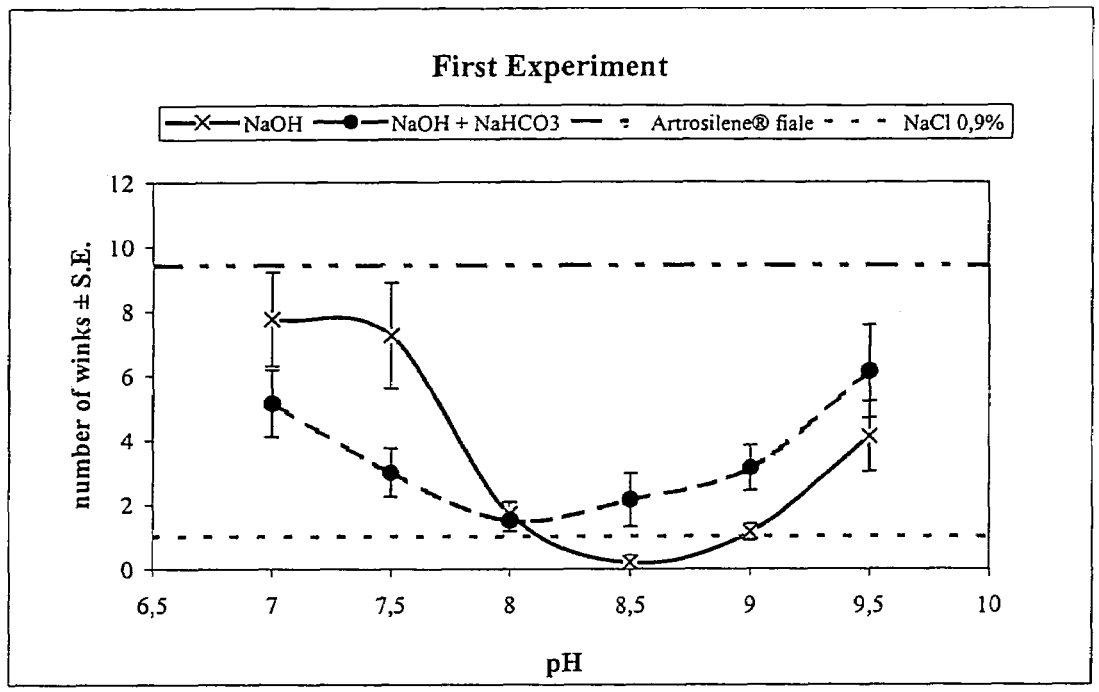
FIGS. 1 and 2 show the results of two independent experiments using the rat wink test to evaluate the painfulness of injection of compositions over various pH.

The present invention thus provides a pharmaceutical composition suitable for parenteral administration having anti-inflammatory and analgesic property, characterized in that it contains an alkylammonium salt of a 2-arylpropionic acid selected from ketoprofen, ibuprofen, naproxen or tiaprofenic acid, in racemic or in enantiomeric form, in an aqueous solution at a pH in the range between 8 and 9, said solution being free of preservatives, co-solvents and supporting substances. Preferred compositions contain ketoprofen as a salt of L-lysine.

More preferred compositions contain ketoprofen L-lysine salt, sodium bicarbonate and sodium hydroxide at pH 8.5.

DETAILED DESCRIPTION OF THE INVENTION

Different formulations of ketoprofen L-lysine salt in aqueous solution at different pH have been prepared and tested in the rat wink test as defined above. Suitable formulations have been selected from this assay and compared with classical ketoprofen Formulations at pH .6.5 and with the commercial preparation of ketoprofen "Artrosilene® fiale". Solutions in a range of pH between 8 and 9 have not caused any pain upon injection and have been shown to be much better than Artrosilene® in this respect.

A correlation between the rat wink test and the clinical test based on the VAS value has also been found.

Materials used in the experiments are reported in Table 1:

TABLE 1

| | Supplier |
|---|---|
| Ketoprofen lysine salt | Dompé |
| NaOH 1N | Riedel-de Haën |
| HCl 35% | Carlo Erba |
| NaHCO$_3$ | G. Faravelli |
| HaCl 0.9% solution | Bieffe Medital |
| Artrosilene ® fiale | Dompé farmaceutici S.p.A. |
| Water for injectable preparations | Bieffe Medital |

All formulations tested are 8% aqueous solutions of ketoprofen L-lysine salt. Solutions with different pH have been prepared, using a NaOH 1N solution, or a HCl 35% solution to adjust pH. In some preparations NaHCO$_3$ was also added at the concentration of 4 mg/mL.

Artrosilene® and NaCl 0.9% solution were extracted from their original ampoules and bottles and were packaged in dark glass vials provided with polymeric cap and aluminium ring. The specific composition, pH and osmolality of the formulations tested in two different experiments are reported in Tables 2 and 3.

TABLE 2

First Experiment

| Batch | Composition | pH | Osmolality (mOsmol/kg) |
|---|---|---|---|
| PG054/34/SU01 | KSL + HCl | 7.0 | 308 |
| PG054/35/SU01 | KSL | 7.2 | 267 |
| PG054/36/SU01 | KSL + NaOH | 8.0 | 289 |
| PG054/37/SU01 | KSL + NaOH | 9.0 | 333 |
| PG054/38/SU01 | KSL + NaOH | 9.5 | 403 |
| PG054/53/SU01 | KSL + NaOH | 8.5 | 382 |
| PG054/45/SU01 | KSL + NaHCO$_3$ | 7.0 | 359 |
| PG054/46/SU01 | KSL + NaHCO$_3$ + NaOH | 7.5 | 351 |
| PG054/47/SU01 | KSL + NaHCO$_3$ + NaOH | 8.0 | 358 |
| PG054/48/SU01 | KSL + NaHCO$_3$ + NaOH | 8.5 | 382 |
| PG054/49/SU01 | KSL + NaHCO$_3$ + NaOH | 9.0 | 395 |
| PG054/50/SU01 | KSL + NaHCO$_3$ + NaOH | 9.5 | 455 |

TABLE 3

Second Experiment

| Batch | Composition | pH | Osmolality (mOsmol/kg) |
|---|---|---|---|
| PG054/62/SU01 | KSL + NaHCO$_3$ + HCl | 7.0 | 356 |
| PG054/63/SU01 | KSL + HCl | 7.0 | 276 |
| PG054/64/SU01 | KSL + NaHCO$_3$ + NaOH | 8.0 | 362 |
| PG054/65/SU01 | KSL + NaOH | 8.0 | 282 |
| PG054/66/SU01 | KSL + NaHCO$_3$ + NaOH | 9.0 | 399 |
| PG054/67/SU01 | KSL + NaOH | 9.0 | 336 |
| PG054/70/SU01 | KSL + NaOH | 7.5 | 268 |
| PG054/71/SU01 | KSL + NaOH | 8.5 | 301 |
| PG054/72/SU01 | KSL + NaOH | 9.5 | 405 |
| PG054/75/SU01 | KSL + NaHCO$_3$ + NaOH | 7.5 | 354 |
| PG054/76/SU01 | KSL + NaHCO$_3$ + NaOH | 8.5 | 384 |
| PG054/77/SU01 | KSL + NaHCO$_3$ + NaOH | 9.5 | 463 |

Animals

The animals used in the experiments are described herebelow:

Species: rat

Strain: Sprague-Dawley

Supplier: Charles-River (Calco, LC, Italy)

Sex: male

Age: 5-7 weeks

Body weight at arrival: 176-200 g

On arrival the animals were housed five per cage (Makrolon® 3G type, Tecniplast Gazzada S.r.l., Buguggiate, VA, Italy) and acclimated for at least 6 days in the animal room.

Poplar and fir chips, heat-processed for resin removal and dust-free, were used for bedding.

Contaminants that might interfere with the purpose of the study, were not expected to be present in the wood.

Animal room temperature was 20° C.±2 and relative humidity was 55%±10.

Room illumination: 12-hour artificial light (7.00 am-7.00 pm), 12-hour dark (7.00 pm-7.00 am).

The animals were feeded with pellets provided by Laboratorio Dottori Piccioni, Gessate, Milano, Italy. According to the analytical certificates provided by the supplier, the contents of contaminants were within the limits proposed by EPA-TSCA (44 Fed. Reg. 44053-44093 Jul. 26, 1979).

Contaminants that might interfere with the purpose of the study were not expected to be present either in the diet or in the water provided to the animals.

Food and water were supplied ad libitum during acclimatisation.

The different formulations of ketoprofen were administered in the eye of each animal and the number of winks in each case was determined in a fixed amount of time. In all experiments 25 µL of each formulation were instilled in the rat's eye using a Gilson pipette.

| Formulation | |
|---|---|
| ketoprofen L-lysine salt | 160 mg |
| sodium bicarbonate | 8 mg |
| sodium hydroxide | 3 mg |
| water for injection q.s. | 2 ml |

Preparation Method 160 mg of ketoprofen L-lysine salt and 3 mg of sodium hydroxide are added to 1.6 ml of water for injection. Sodium bicarbonate (8 mg) is than added to the solution, then water for injection is added up to 2 ml.

EXAMPLE 1

Rat Wink Test

In the first session of each experiment, 25 µL of each formulation were instilled into rats' left eye. In the second session 25 µL of each formulation were instilled in the same rats' right eye.

In each session, rats' winks were counted within 15 seconds from instillation (time was taken by means of a chronometer).

The time elapsed between the two experiments was 8 days.

Results of the first experiment are reported in Tables 4 and 5. FIG. 1 outlines the pH-response profile observed in the first experiment.

Figure 2:
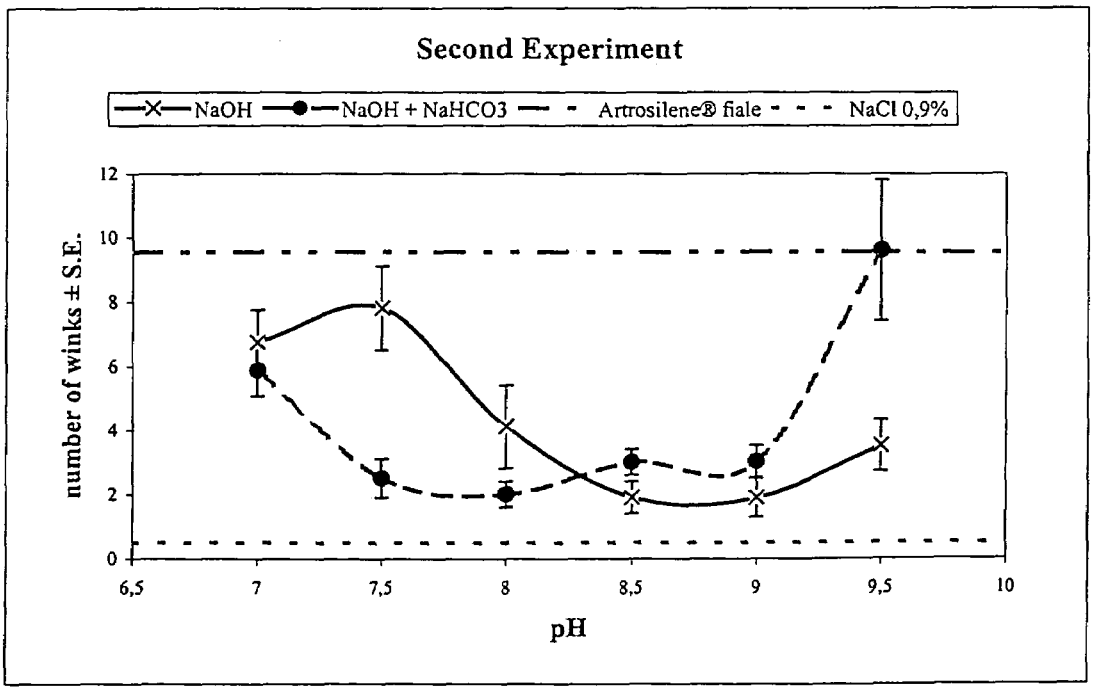

Results of the second experiment are reported in Tables 6 and 7. FIG. 2 outlines the pH-response profile observed in the second experiment.

TABLE 4

First session - First experiment

| Batch | Composition | pH | Osmolality (mOsmol/kg) | Mean of winks After 15" from instillation | Standard Error |
|---|---|---|---|---|---|
| PG054/34 | KSL + HCl | 7.0 | 308 | 7.75 | 1.4 |
| PG054/35 | KSL | 7.2 | 267 | 7.25 | 1.6 |
| PG054/36 | KSL + NaOH | 8.0 | 289 | 1.71 | 0.4 |
| PG054/37 | KSL + NaOH | 9.0 | 333 | 1.14 | 0.3 |
| PG054/38 | KSL + NaOH | 9.5 | 403 | 4.13 | 1.1 |
| PG054/53 | KSL + NaOH | 8.5 | 301 | 0.2 | 0.2 |
| PG054/40 | Artrosilene ® fiale | 7.3 | 308 | 9.25 | 1.9 |
| PG054/41 | NaCl | — | — | 0.83 | 0.4 |

TABLE 5

Second session - First experiment

| Batch | Composition | pH | Osmolality (mOsmol/kg) | Mean of winks After 15" from Instillation | Standard Error |
|---|---|---|---|---|---|
| PG054/45 | KSL + NaHCO$_3$ | 7.0 | 359 | 5.1 | 1.0 |
| PG054/46 | KSL + NaHCO$_3$ + NaOH | 7.5 | 351 | 3.0 | 0.8 |
| PG054/47 | KSL + NaHCO$_3$ + NaOH | 8.0 | 358 | 1.5 | 0.3 |
| PG054/48 | KSL + NaHCO$_3$ + NaOH | 8.5 | 382 | 2.1 | 0.8 |
| PG054/49 | KSL + NaHCO$_3$ + NaOH | 9.0 | 395 | 3.1 | 0.7 |
| PG054/50 | KSL + NaHCO$_3$ + NaOH | 9.5 | 455 | 6.1 | 1.4 |
| PG054/51 | Artrosilene ® fiale | 7.4 | 307 | 9.6 | 2.5 |
| PG054/52 | NaCl | — | — | 1.2 | 0.6 |

TABLE 6

First session - Second experiment

| Batch | Composition | pH | Osmolality (mOsmol/kg) | Mean of winks after 15" from instillation | Standard Error |
|---|---|---|---|---|---|
| PG054/62 | KSL + NaHCO$_3$ + HCl | 7.0 | 356 | 5.9 | 0.8 |
| PG054/63 | KSL + HCl | 7.0 | 276 | 6.8 | 1.0 |
| PG054/64 | KSL + NaHCO$_3$ + NaOH | 8.0 | 362 | 2.0 | 0.4 |
| PG054/65 | KSL + NaOH | 8.0 | 282 | 4.1 | 1.3 |
| PG054/66 | KSL + NaHCO$_3$ + NaOH | 9.0 | 399 | 3.0 | 0.5 |
| PG054/67 | KSL + NaOH | 9.0 | 336 | 1.9 | 0.6 |
| PG054/68 | Artrosilene ® fiale | 7.3 | — | 10.3 | 1.7 |
| PG054/69 | NaCl | — | — | 0.4 | 0.2 |

TABLE 7

Second session - Second experiment

| Batch | Composition | pH | Osmolality (mOsmol/kg) | Mean of winks after 15" from instillation | Standard Error |
|---|---|---|---|---|---|
| PG054/70 | KSL + NaOH | 7.5 | 268 | 7.8 | 1.3 |
| PG054/71 | KSL + NaOH | 8.5 | 301 | 1.9 | 0.5 |
| PG054/72 | KSL + NaOH | 9.5 | 405 | 3.5 | 0.8 |
| PG054/73 | Artrosilene ® fiale | 7.3 | 282 | 8.8 | 1.7 |
| PG054/74 | NaCl | — | 308 | 0.6 | 0.2 |
| PG054/75 | KSL + NaHCO$_3$ + NaOH | 7.5 | 354 | 2.5 | 0.6 |
| PG054/76 | KSL + NaHCO$_3$ + NaOH | 8.5 | 384 | 3.0 | 0.4 |
| PG054/77 | KSL + NaHCO$_3$ + NaOH | 9.5 | 463 | 9.6 | 2.2 |

VAS Evaluation

All clinical trials were performed by LCG (Bourn Hall Clinic, Cambridge, UK), except clinical trial KLS 0497 performed by Aster Clinical Research Center (Paris France), and clinical trial KLS 0101 performed by I.P.A.S. S.A. (Ligornetto, Switzerland).

Each treatment consisted in a deep intramuscular injection of one ampoule of test formulations in the upper outer quarter of the gluteus maximus. Each injection was performed within 10 minutes after preparation of the syringe and lasted 3-5 seconds. The intensity of pain at the injection site was evaluated by subjects and recorded on case report forms using the 100 mm Visual Analogue Scale.

Statistical elaboration was performed by STAT100 release 1.26 for Windows 95. Data are imported in statistical software from Microsoft Excel by means of copy/paste function, printed and manually checked before starting the elaboration. All variables were described with N, mean, standard deviation, standard error of the mean.

't-test' was performed to compare the reference compound (Artrosilene®) against saline to verify the efficiency of the test.

ANOVA (One Way replicated measures) was performed to compare the pH-response profile of ketoprofen. Dunnett's test was applied.

Results are reported in Table 8, where VAS numbers are compared with rat winks numbers.

A correlation between the number of winks in rats and VAS (Visual Analogue Scale) number in humans has in fact been confirmed in our experiments.

Table 8 reports a summary of the results achieved with different formulations (relevant compositions are reported in Table 9). VAS number was taken immediately after injection, while rat winks were counted 15 seconds after instillation in rat's eye.

Figure 3:
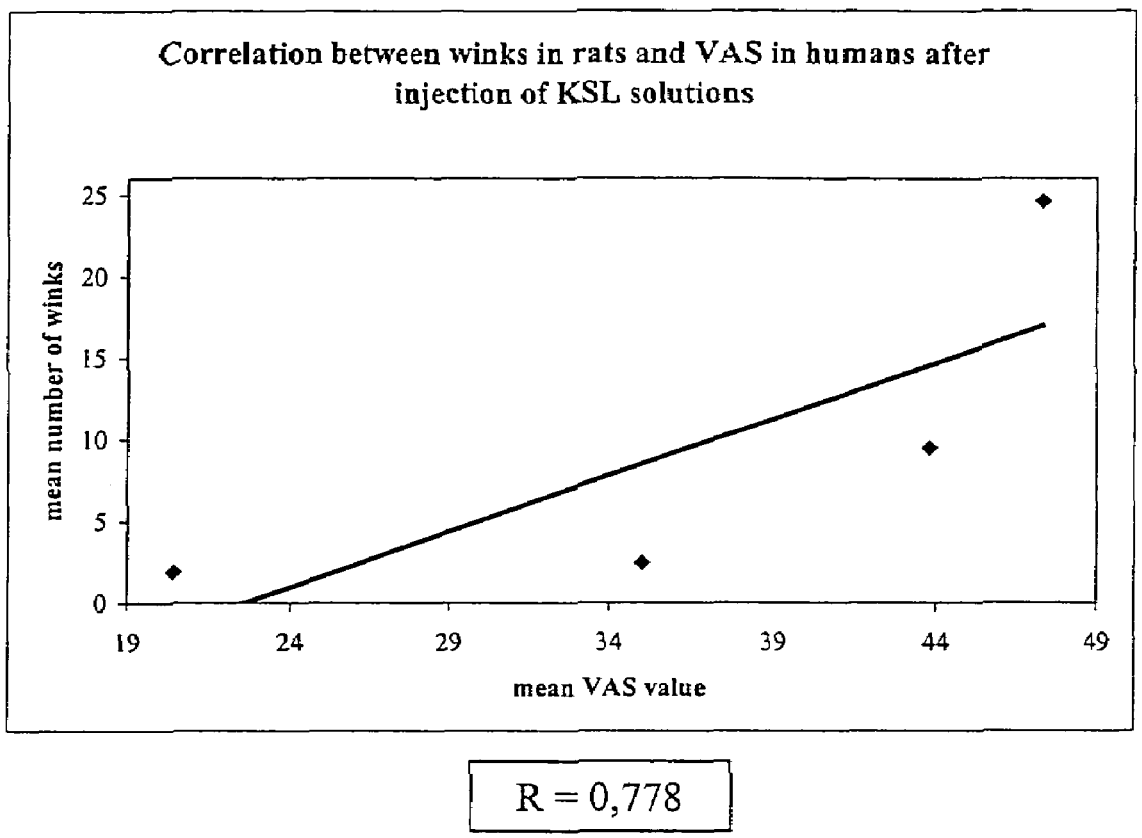
FIG. 3 shows the correlation between the results of rat wink test experiments and the visual analog scale test of pain experience performed in humans.

The correlation between VAS and number of winks in rats after administration of the same formulations is outlined in FIG. 3.

Aqueous formulations of ketoprofen lysine salt (KSL) (80 mg/mL) and KSL formulations (80 nmg/mL) containing sodium bicarbonate (4 mg/mL) with pH in the range between 7.0 and 9.5 were tested. As a reference standard Artrosilene® fiale and a sodium chloride 0.9% solution were used. Results in the rat wink test showed that the number of winks was higher for the formulations with a pH value at the extreme limit of the investigated range.

The concave-shaped curve obtained from these experiments showed that formulations with intermediate pH value were better tolerated (i.e. the number of winks are closer to the value obtained with the saline isotonic solution).

An aqueous solution of KSL showed a minimum value at pH 8.5, with lower winking values in the range of pH between 8.0 and 9.5.

The aqueous solution of KSL+sodium bicarbonate showed the minimum winking effect at pH 8.0, with lower values in the pH range between 7.5 and 9.0. The experiment was performed in duplicate, testing formulations with the sane compositions, but of different batches, obtaining the same results in both experimental sets.

From an analysis of experimental data we have observed that the winks number caused by formulations with a pH in the range between 8.0 and 9.0 (KSL solutions and KSL+bicarbonate solutions) was comparably lower. In this pH range the effect on the reduction of the number of winks was significant. On the other side the osmolality didn't seem to have an effect on winks number.

In the second part of the study, the number of winks of KSL formulations was related to the VAS obtained testing in human the same formulations. A correlation with R=0.778 was found and it was noticed that formulations with higher

TABLE 8

| Formulation* | Clinic N° | N° of patients | Mean VAS value ± S.D. | N° of patients with VAS ≧ 50 | N° of patients with VAS ≧ 75 | Mean winks number |
|---|---|---|---|---|---|---|
| KSL + Phosphate buffer pH 6.5 | KSL0199 | 48 | 47.3 ± 26.3 | 22 (45.83%) | 7 (14.58%) | 24.6 |
| Artrosilene ® fiale pH 7.0 | KSL0196 | 18 | 46.9 ± 25.6 | 9 (50%) | 4 (22.22%) | 9.49 |
| Artrosilene ® fiale pH 7.0 | KSL0396 | 17 | 45.3 ± 23.5 | 7 (41.18%) | 3 (17.65%) | |
| Artrosilene ® fiale pH 7.0 | KSL0497 | 31 | 42.9 ± 21.2 | 12 (38.71%) | 3 (9.68%) | |
| Artrosilene ® fiale pH 7.0 | KSL0199 | 44 | 40.0 ± 27.0 | 15 (34.09%) | 6 (13.64%) | |
| KSL + NaHCO$_3$ pH 8.0 | KSL0100 | 12 | 35.0 ± 25.3 | 4 (33.33%) | 1 (8.33%) | 2.45 |
| KSL + NaHCO$_3$ PH 8.5 | KSL0101 | 32 | 20.4 ± 16.2 | 2 (6.25%) | 0 | 1.9 |

TABLE 9

Composition of formulations

| KSL + phosphate buffer pH 6.5 | Artrosilene ® fiale pH 7.0 | KSL + NaHCO$_3$ pH 8.0 | KSL + NaHCO$_3$ pH 8.5 |
|---|---|---|---|
| KSL 160 mg | KSL 160 mg | KSL 160 mg | KSL 160 mg |
| NaH$_2$PO$_4$.H$_2$O 35.88 mg | Citric acid anhydrous 5 mg | NaHCO$_3$ 4 mg | NaHCO$_3$ 8 mg |
| NaOH q.s. to pH 6.5 | NaOH q.s. to pH 7.0 | NaOH q.s. to pH 8.0 | NaOH q.s. to pH 8.5 |
| Water for injection q.s. to 2 mL | Water for injection q.s. to 2 mL | Water for injection q.s. to 2 mL | Water for injection q.s. to 2 mL | pH were also better tolerated in humans showing lower VAS values. In fact, focusing on the formulation at pH 8.5, it was found, as it is shown on the table 8, that its mean VAS value (20.4) is much lower than Artrosilene® fiale formulation (mean: 43.8). Moreover, 6.25% of the patients treated with pH 8.5 formulation showed a VAS value≧50 and no patient showed a VAS number≧75, while 41% of patients to whom Artrosilene® fiale was injected showed a VAS value≧50 and 15.8% showed a VAS≧75.

As shown in table 8, the VAS values of Artrosilene obtained from different clinical trials and performed in different clinical centres, are comparable.

This result was confirmed by winking test. In fact for Artrosilene® fiale a winking number of 9.49 was found, remarkably higher than 1.9 value found for the formulation at pH 8.5.

Considering the results obtained in the rat wink test and the correlation between VAS and winks number, we conclude that formulations with pH in the range between 8.0 and 9.0 are less painful. The preferred formulation which causes no pain upon injection is then an aqueous formulation having a pH of about 8.5.

The invention claimed is:

1. A pharmaceutical composition having anti-inflammatory and analgesic property, comprising an alkylammonium salt of a 2-arylpropionic acid which is a L-lysine salt of ketoprofen in an aqueous solution at a pH in the range from 8 to 9, said solution being free of preservatives and co-solvents, wherein the composition is formulated for parenteral administration.

2. The pharmaceutical composition of claim 1, further comprising sodium bicarbonate.

3. The pharmaceutical composition of claim 2, wherein the concentration of said sodium carbonate is 4 mg/ml.

4. The pharmaceutical composition of claim 1, further comprising sodium hydroxide.

5. The pharmaceutical composition of claim 4, wherein the concentration of said sodium hydroxide is 1.5 mg/ml.

* * * * *